(12) United States Patent
Byrd et al.

(10) Patent No.: US 8,888,856 B2
(45) Date of Patent: Nov. 18, 2014

(54) TOTAL KNEE IMPLANT

(75) Inventors: Christopher M. Byrd, Elkhart, IN (US); Adam H. Sanford, Warsaw, IN (US); Brian D. Earl, South Bend, IN (US); Jody L. Claypool, Columbia City, IN (US); Jeffrey D. Brown, Palo Alto, CA (US); John E. Pendleton, Dunwoody, GA (US)

(73) Assignee: Zimmer, Inc., Warsaw, IN (US)

(*) Notice: Subject to any disclaimer, the term of this patent is extended or adjusted under 35 U.S.C. 154(b) by 319 days.

(21) Appl. No.: 12/694,343

(22) Filed: Jan. 27, 2010

(65) Prior Publication Data
US 2010/0191342 A1    Jul. 29, 2010

Related U.S. Application Data

(60) Provisional application No. 61/147,492, filed on Jan. 27, 2009.

(51) Int. Cl.
| | | |
|---|---|---|
| *A61F 2/38* | (2006.01) | |
| *A61F 2/08* | (2006.01) | |
| *A61F 2/30* | (2006.01) | |
| *A61F 2/46* | (2006.01) | |

(52) U.S. Cl.
CPC ..... *A61F 2/3868* (2013.01); *A61F 2002/30462* (2013.01); *A61F 2002/30466* (2013.01); *A61F 2220/0025* (2013.01); *A61F 2002/4666* (2013.01); *A61F 2/3836* (2013.01); *A61F 2002/3895* (2013.01); *A61F 2220/0075* (2013.01); *A61F 2250/0018* (2013.01); *A61F 2002/30014* (2013.01); *A61F 2/4684* (2013.01); *A61F 2/468* (2013.01); *A61F 2002/30387* (2013.01); *A61F 2/08* (2013.01); *A61F 2002/304* (2013.01)
USPC ..................................................... 623/20.14

(58) Field of Classification Search
CPC .. A61B 17/154; A61B 17/155; A61B 17/157; A61B 17/1659; A61B 17/1675; A61B 17/686; A61B 2019/461; A61B 17/00234; A61B 17/025; A61B 17/1764; A61B 17/1767; A61B 17/70; A61B 19/46; A61B 2017/00004; A61B 2017/00557
USPC ........................................... 623/20.14–20.36
See application file for complete search history.

(56) References Cited

U.S. PATENT DOCUMENTS 5,282,867 A * 2/1994 Mikhail ...................... 623/13.12
5,374,269 A   12/1994 Rosenberg
(Continued)

FOREIGN PATENT DOCUMENTS

| EP | 0447065 A2 | 9/1991 |
|---|---|---|
| EP | 1159938 A1 | 4/2001 |

OTHER PUBLICATIONS

The International Preliminary Report on Patentability issued Aug. 2, 2011 in the related International Application No. PCT/US2010/022163.

(Continued)

*Primary Examiner* — David Isabella
*Assistant Examiner* — Ann Schillinger
(74) *Attorney, Agent, or Firm* — Schwegman Lundberg & Woessner, P.A.

(57) ABSTRACT

A knee prosthesis is provided for use in knee arthroplasty. In one exemplary embodiment, the present invention provides a tibial prosthesis having a tibial baseplate with a fixed medial bearing component and a mobile lateral bearing component. In one exemplary embodiment, the lateral bearing component is secured to the lateral portion of the tibial baseplate utilizing at least one prosthetic ligament. Additionally, in one exemplary embodiment, a stop is provided to limit anterior or posterior movement of the lateral bearing component relative to the tibial baseplate. For example, the stop may be defined by cooperating shoulders formed on the lateral bearing and the tibial baseplate.

13 Claims, 9 Drawing Sheets

(56) References Cited

U.S. PATENT DOCUMENTS

| | | | |
|---|---|---|---|
| 5,570,706 | A | 11/1996 | Howell |
| 5,601,562 | A | 2/1997 | Wolf et al. |
| 5,769,894 | A | 6/1998 | Ferragamo |
| 5,957,979 | A * | 9/1999 | Beckman et al. ......... 623/20.33 |
| 6,013,103 | A | 1/2000 | Kaufman et al. |
| 6,905,513 | B1 | 6/2005 | Metzger |
| 7,032,599 | B2 | 4/2006 | May et al. |
| 7,153,327 | B1 | 12/2006 | Metzger |
| 7,255,715 | B2 | 8/2007 | Metzger |
| 2004/0193279 | A1 | 9/2004 | Roger |
| 2005/0187635 | A1 | 8/2005 | Metzger |
| 2005/0222574 | A1 | 10/2005 | Giordano et al. |
| 2006/0116684 | A1 | 6/2006 | Whelan |
| 2006/0149259 | A1 | 7/2006 | May et al. |
| 2006/0149283 | A1 | 7/2006 | May et al. |
| 2007/0010884 | A1 | 1/2007 | Tuke |
| 2009/0306784 | A1 | 12/2009 | Blum |

OTHER PUBLICATIONS

The partial search report mailed Apr. 29, 2010, in related International Application No. PCT/US010/022163.

Written Opinion and International Search Report mailed Aug. 19, 2010 in related International Application No. PCT/US2010/022163.

\* cited by examiner

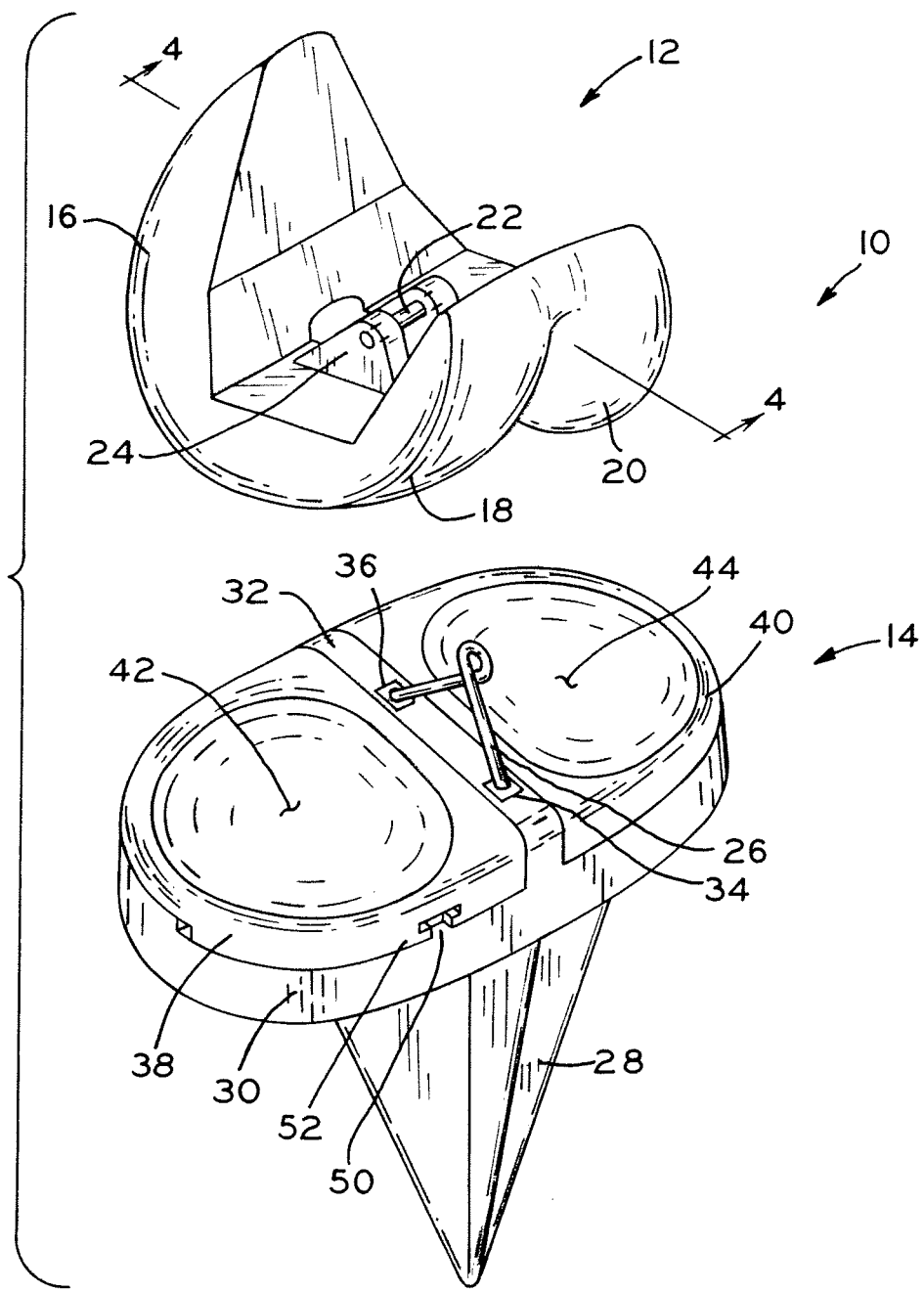
FIG_1

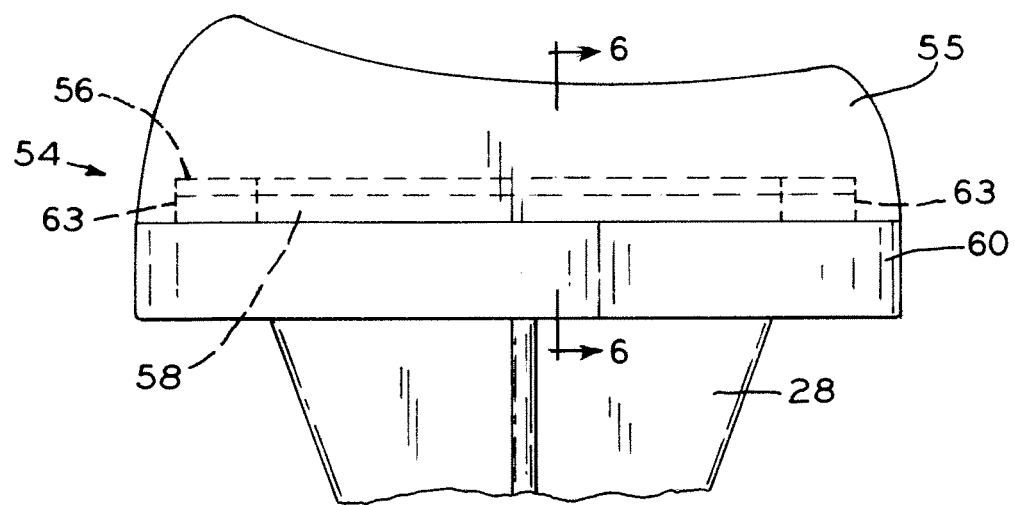
FIG_5
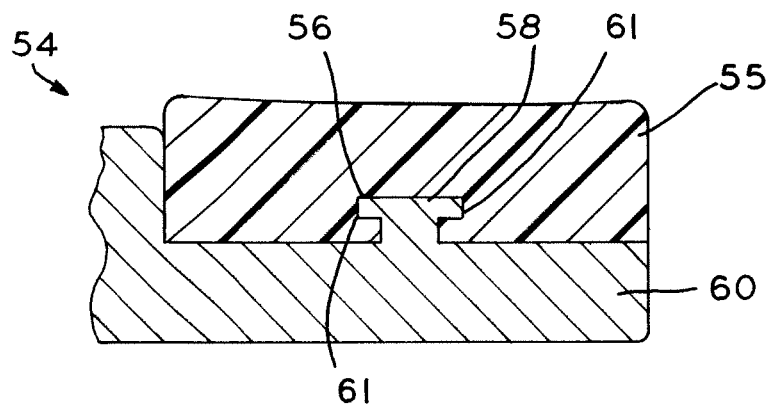
FIG_6

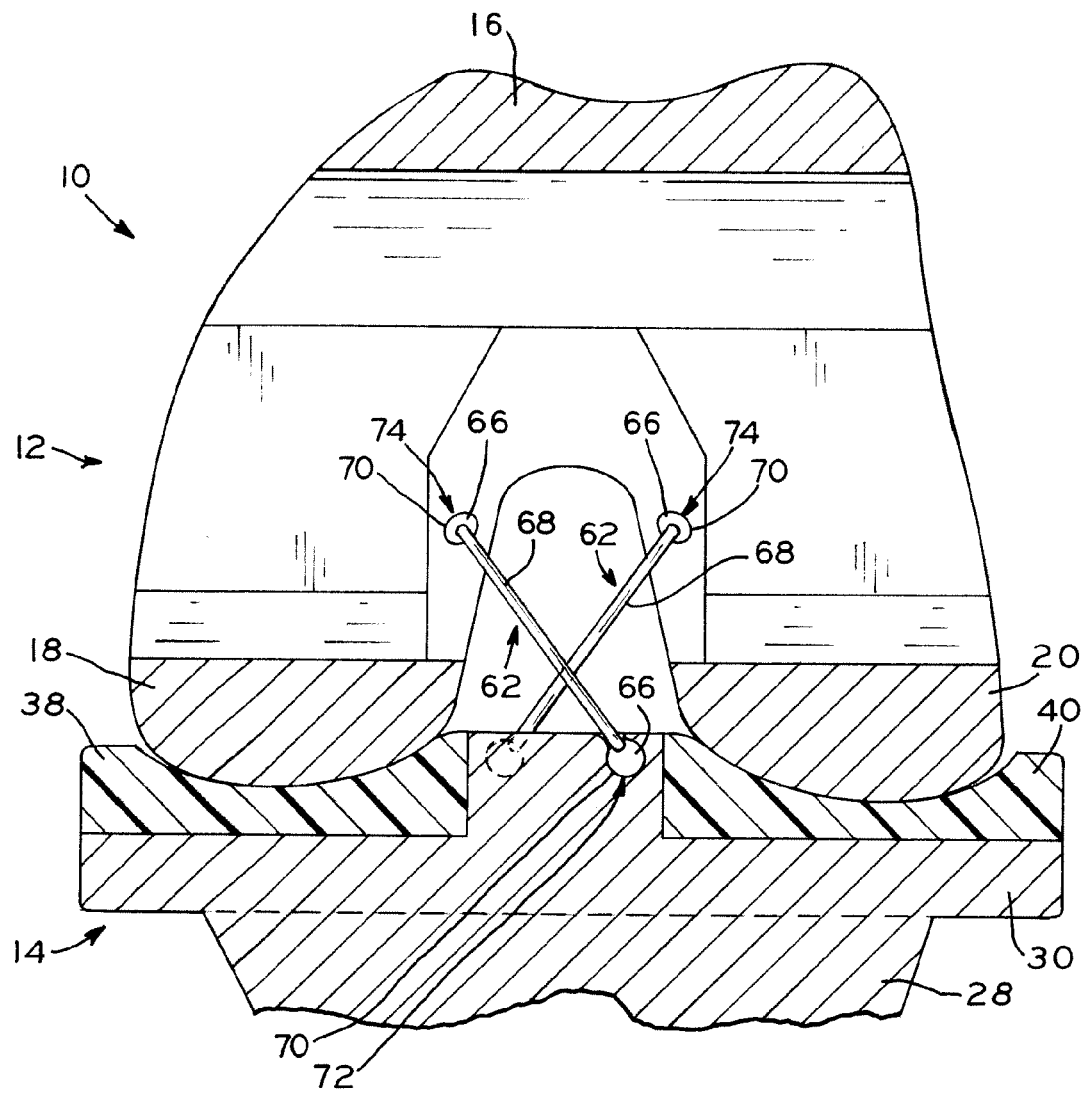
FIG_7

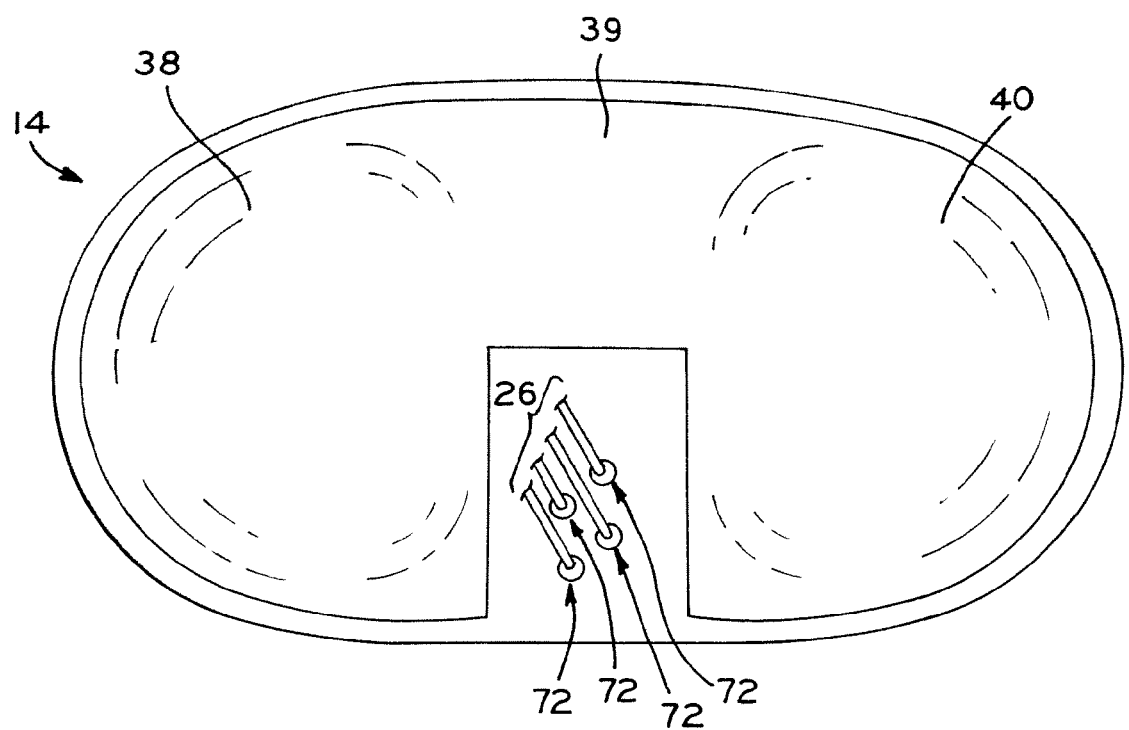
FIG_9B

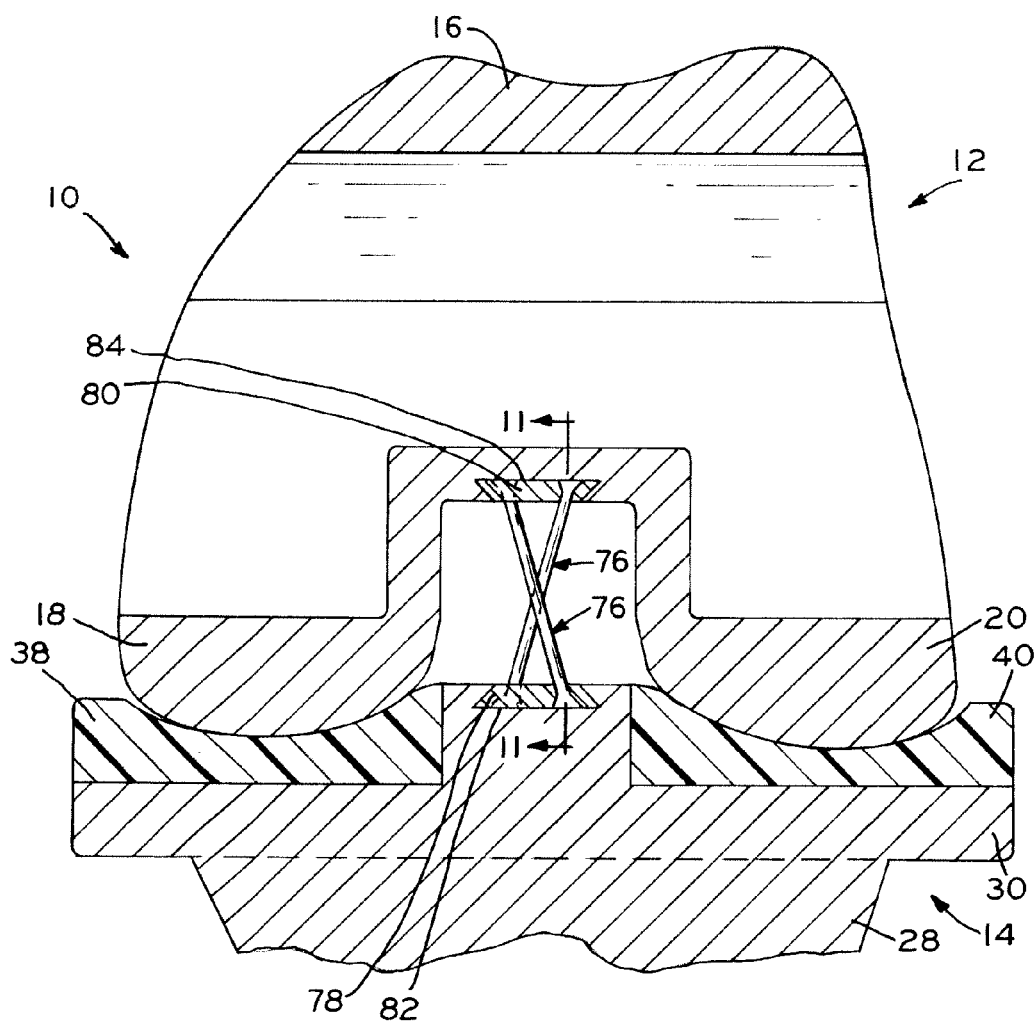
FIG_10
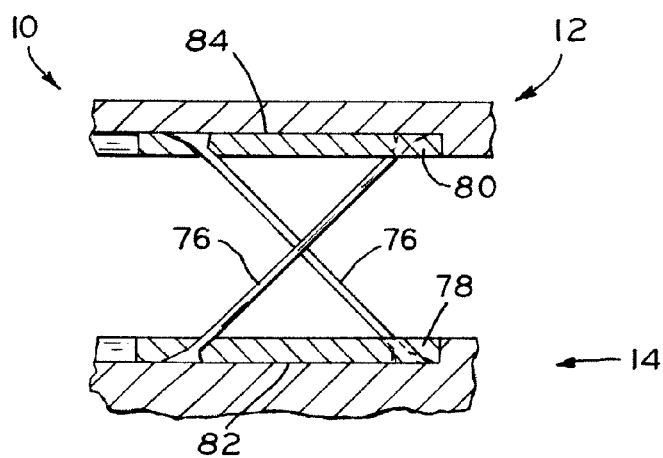
FIG_11

TOTAL KNEE IMPLANT

CROSS REFERENCE TO RELATED APPLICATION

This application claims the benefit under Title 35, U.S.C. §119(e) of U.S. Provisional Patent Application Ser. No. 61/147,492, entitled TOTAL KNEE IMPLANT, filed on Jan. 27, 2009, the entire disclosure of which is expressly incorporated herein by reference.

BACKGROUND

1. Field of the Invention

The present invention relates to orthopedic prostheses and, particularly, to knee prostheses.

2. Description of the Related Art

In a natural knee joint, the meniscus is positioned between the distal end of the femur and the proximal end of the tibia to provide cushioning and support to the tibia and femur as they rotate relative to one another. Additionally, the medial side of the meniscus is more stationary than the lateral side of the meniscus, which is more flexible and/or mobile. The mobility of the lateral meniscus increases the ability of the lateral condyle of the femur to roll off of the tibial plateau during high flexion of the knee, i.e., it increases the ability of the femur to rotate into a position in which the lateral condyle is not entirely supported by the tibial plateau.

In a fixed bearing tibial prosthesis, external rotation of the femoral component against the tibial component can be limited due to the fixed nature of the prosthesis. Thus, the lateral condyle of the femur is prevented from rolling off the tibial plateau. In order to provide for articulation of the knee joint that better replicates the natural articulation of the knee joint, a mobile bearing tibial prosthesis may be used. In a mobile bearing tibial prosthesis, the entirety of the tibial bearing, including both the medial and lateral condyles, is rotatable relative to a tibial baseplate. Additionally, in some mobile bearing tibial prostheses, the tibial bearing is rotatable about a point positioned on the medial condyle of the tibial baseplate. This results in increased lateral rotation of the bearing component, which better mimics natural knee joint articulation.

Additionally, during a total knee arthroplasty, it may be necessary to resect the cruciate ligaments of the knee joint. This may result, for example, in decreased support and stability in the patient's knee joint.

SUMMARY

The present disclosure provides knee prostheses for use in knee arthroplasty. In one exemplary embodiment, the present invention provides a tibial prosthesis having a tibial baseplate with a fixed medial bearing component and a mobile lateral bearing component. In one exemplary embodiment, the lateral bearing component is secured to the lateral portion of the tibial baseplate utilizing at least one prosthetic ligament. Additionally, in one exemplary embodiment, a stop is provided to limit anterior or posterior movement of the lateral bearing component relative to the tibial baseplate. For example, the stop may be defined by cooperating shoulders formed on the lateral bearing and the tibial baseplate.

By providing a fixed medial component and a mobile lateral component for a tibial prosthesis, an articulating surface of a medial condyle of a femoral component may be highly conforming with an articulating surface on the medial component of the tibial prosthesis, which acts to control anterior and posterior movement of the joint. Additionally, the mobile lateral component of the tibial component allows for a lateral condyle on a femoral component to undergo additional rollback, which is normally prevented in both fixed and mobile tibial prostheses, in order to more accurately replicate the natural articulation of the knee joint.

In one exemplary embodiment, the present invention also includes a femoral component. In one exemplary embodiment, the femoral component includes a crossbar extending between opposing medial and lateral condyles. In this embodiment, a prosthetic ligament is wrapped around the crossbar and secured to attachment points on the tibial baseplate. The prosthetic ligament acts to replicate the function of the patient's resected anterior cruciate ligament (ACL) by restricting movement of the femoral component relative to the tibial component. In other exemplary embodiments, a plurality of prosthetic ligaments may be provided that are configured for attachment to a plurality of attachment points on the tibial baseplate and femoral components. In this manner, by selectively positioning the prosthetic ligaments with respect to the femoral component and tibial baseplate, the natural articulation of the knee joint for an individual patient may be more accurately replicated.

In other exemplary embodiments, provisional prosthetic ligaments may be utilized to facilitate the trialing of the femoral component and the tibial component. For example, in one exemplary embodiment, the provisional prosthetic ligaments are designed to fail if the ligaments are subjected to a tension that exceeds a predetermined tension limit. In one exemplary embodiment, opposing portions of the provisional prosthetic ligaments may be secured to one another by magnets. Once a tension that exceeds the predetermined amount of tension is applied to the ligaments, the magnetic force between the two magnets that holds the opposing portions of the ligaments together is overcome, causing the ligaments to fail. This allows a surgeon to trial the prosthetic component and, if the ligaments fail, the surgeon is provided with a visual and tactile indication that the patient's knee joint is too tight. In other exemplary embodiments, the provisional prosthetic ligaments may be designed to break if a tension in excess of a predetermined tension limit is applied to the ligaments. In another exemplary embodiment, the provisional prosthetic ligaments may be designed to separate from one of the femoral component and tibial component if a tension is applied to the ligaments that exceeds a predetermined amount of tension.

Additionally, by allowing for the use of prosthetic ligaments, the ability of a surgeon to replicate the natural articulation of a knee joint for a particular patient is increased. For example, when a plurality of attachment sites are provided on the tibial and/or femoral components, the surgeon may individually select attachment sites based on specific physical characteristics of an individual patient. As a result, the surgeon may more accurately replicate the natural knee articulation for an individual patient. Further, by providing provisional prosthetic ligaments that allow for separation and/or failure of the provisional prosthetic ligaments if a tension that exceeds a predetermined tension is applied to the provisional prosthetic ligaments, the surgeon may also test the knee joint to determine whether the joint is too tight. The provisional prosthetic ligaments provide a visual and/or tactile feedback that immediately indicates whether the joint is too tight.

In one form thereof, the present invention provides a prosthetic knee system including a femoral component having a lateral condyle and a medial condyle and a tibial component having a base plate, a medial bearing surface and a lateral bearing surface. The baseplate includes a bone facing surface and an opposing support surface. The medial bearing component includes a medial articulation surface and a medial attachment surface, with the medial attachment surface coupled with the support surface of the baseplate to fix the medial component to the baseplate, so that movement of said medial component relative to said baseplate is substantially entirely prevented. The lateral bearing component includes a lateral articulation surface and a lateral attachment surface, with the lateral attachment surface slidingly secured to the support surface of the baseplate. The lateral component is translatable relative to the baseplate.

In one aspect, a T-shaped projection may be formed on either the lateral attachment surface of the lateral component or the support surface of the baseplate, with a T-shaped groove formed on the other surface, i.e., the surface without the T-shaped projection. The T-shaped projection may be sized and positioned to cooperate with said T-shaped groove to form a securement mechanism when the lateral attachment surface of the lateral component is slidingly secured to the support surface of the baseplate, with the securement mechanism allowing translation of the lateral component in an anterior direction and a posterior direction.

In another aspect, the baseplate may include a first baseplate shoulder formed on the support surface, and the lateral component may include a first lateral component shoulder formed on the lateral attachment surface. The first baseplate shoulder and the first lateral component shoulder may cooperate to limit either anterior translation or posterior translation of the lateral component.

In yet another aspect, the prosthetic knee system may include a first prosthetic ligament with an elongate body, a first end, and a second end, with the first end and the second end attachable to the tibial component. The femoral component may include a crossbar disposed between the medial condyle and the lateral condyle, with the elongate body of the first prosthetic ligament wrapped around the crossbar to couple the femoral component to the tibial component.

In another form thereof, the present invention provides a prosthetic knee system includes a femoral component, a tibial component and a first prosthetic ligament. The femoral component has a lateral condyle and a medial condyle, and defines at least one femoral attachment point. The tibial component has a lateral articulating surface and a medial articulating surface, and defines at least one tibial attachment point. The first prosthetic ligament having an elongate body, a first end, and a second end, with the first end attachable to the femoral attachment point of the femoral component and the second end attachable to the tibial attachment point of the tibial component, so that the femoral component is coupled with the tibial component when the first prosthetic ligament is attached to the femoral attachment point and the tibial attachment point.

In one aspect, a second prosthetic ligament, or a plurality of prosthetic ligaments may be provided to extend between posterior and/or anterior attachment points on the tibial component and lateral and/or medial attachment points on the femoral component. In another aspect, means for severing the prosthetic ligament may be provided, such as a pair of cooperating magnets disposed a first end and a second end of the prosthetic ligament, a weakened portion along a portion of the elongate body of the first prosthetic ligament, and/or a connection between the prosthetic ligament and the femoral component or the tibial component.

In yet another form thereof, the present invention provides a method of intraoperatively defining tension between components of a prosthetic knee system, the method including: providing a femoral component having a lateral condyle and a medial condyle, the femoral component defining at least one femoral attachment point; providing a tibial component having a lateral articulating surface and a medial articulating surface, the tibial component defining at least one tibial attachment point; attaching a first end of a prosthetic ligament to the femoral attachment point of the femoral component; attaching a second end of the prosthetic ligament to the tibial attachment point of the tibial component; and selecting a tension of the prosthetic ligament.

In one aspect, a plurality of prosthetic ligaments may have first ends attached to respective femoral attachment points, and the plurality of prosthetic ligaments may have second ends attached to respective tibial attachment points. In another aspect, a provisional prosthetic ligament may be attached to the femoral attachment point and tibial attachment point before the prosthetic ligament is attached and a tension thereof is selected. A tension in the provisional prosthetic ligament may be measured.

BRIEF DESCRIPTION OF THE DRAWINGS

The above-mentioned and other features and advantages of this invention, and the manner of attaining them, will become more apparent and the invention itself will be better understood by reference to the following descriptions of embodiments of the invention taken in conjunction with the accompanying drawings, wherein:

FIG. 1 is a perspective view of a tibial component and femoral component of a total knee arthroplasty system;

FIG. 5 is an elevational view of a tibial component according to another exemplary embodiment;

FIG. 6 is a cross-sectional view of the tibial component of FIG. 5 taken along line 6-6 of FIG. 5;

FIG. 7 is a cross-sectional view of a total knee arthroplasty system depicting a femoral component at 90 degrees of flexion with respect to the tibial component, wherein the cross-section is taken in a medial/lateral direction that is slightly posterior relative to the total knee arthroplasty system, and in which prosthetic ligaments according to an exemplary embodiment are also depicted;

FIG. 9B is a plan view of tibial component according to another exemplary embodiment depicting a plurality of prosthetic ligaments connected to a posterior side thereof;

FIG. 10 is a cross-sectional view of a total knee arthroplasty system according to an exemplary embodiment depicting the femoral component in 90° of flexion with respect to the tibial component, wherein the cross-section is taken in a medial/lateral direction that is slightly posterior relative to the total knee arthroplasty system, and in which prosthetic ligaments according to another exemplary embodiment are also depicted;

FIG. 11 is a fragmentary cross-sectional view of the total knee arthroplasty system of FIG. 10 taken along line 11-11 of FIG. 10.

Corresponding reference characters indicate corresponding parts throughout the several views. The exemplifications set out herein illustrate preferred embodiments of the invention and such exemplifications are not to be construed as limiting the scope of the invention in any manner.

DETAILED DESCRIPTION

Figure 3:
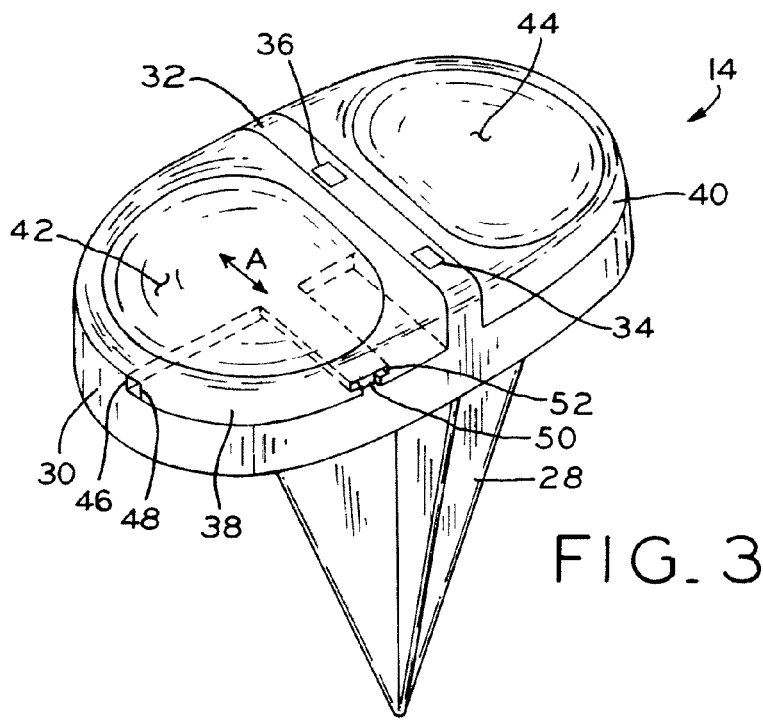
FIG. 3 is a perspective view of the tibial component of the total knee arthroplasty system of FIG. 1.

Referring to FIG. 1, total knee arthroplasty system 10 is shown including femoral component 12 and tibial component 14. Femoral component 12 includes anterior flange 16 and opposing condyles 18, 20, that extend from anterior flange 16. As shown in FIG. 1, total knee arthroplasty system 10 is configured for use in a left knee and, as such, condyle 18 is a lateral condyle and condyle 20 is a medial condyle. However, the principles of the present disclosure are equally applicable to a right or left knee. Extending between opposing condyles 18, 20 is crossbar 22. Crossbar 22 is secured to opposing condyles 18, 20 by base 24 and is designed to receive prosthetic ligament 26 therearound, as defined in detail below. Crossbar 22 may also be integrally formed in base 24, for example.

Figure 4:
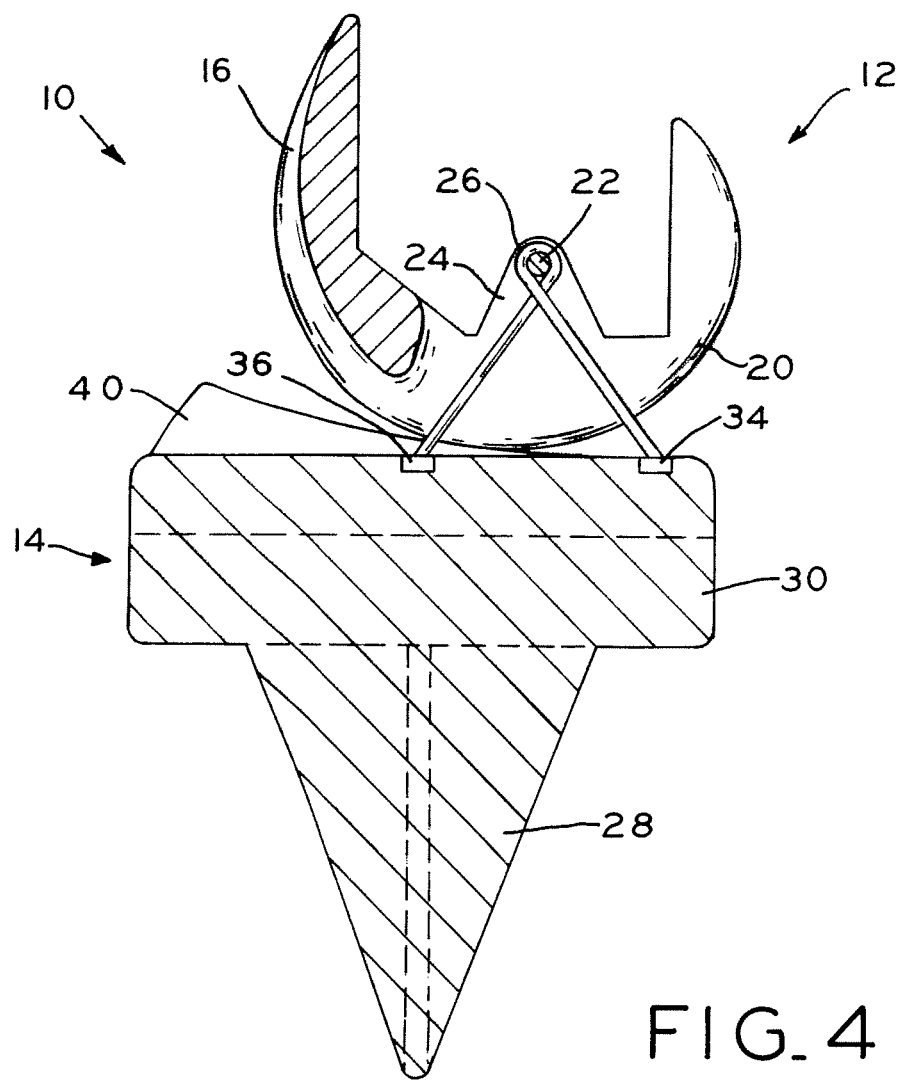
FIG. 4 is a cross-sectional view of the total knee arthroplasty system of FIG. 1, taken along line 4-4 of FIG. 1.

Tibial component 14 includes stem or keel 28 connected to baseplate 30. Tibial component 14 is configured for securement to a resected proximal tibia, such that stem or keel 28 is received within the resected proximal tibia and baseplate 30 sits atop the resected proximal tibia. Extending upward from baseplate 30 is projection 32 that extends in an anterior/posterior direction across tibial component 14 and defines opposing medial and lateral sides of tibial component 14. Projection 32 includes attachment points 34, 36 for receipt of opposing ends of prosthetic ligament 26. When prosthetic ligament 26 is wrapped around crossbar 22 as shown in FIG. 4, affixing ligament 26 to projection 32 via attachment points 34, 36 secures femoral component 12 to tibial component 14. Attachment points 34, 36 may include an adhesive, such as bone cement, to affix ligament 26 to projection 32. However, as described in detail below, various securement methods are available to provide proper affixation of ligament 26 to tibial component 14, as well as to impart a desired tension between femoral component 12 and tibial component 14. For example, multiple prosthetic ligaments 26 may be secured to femoral component 12 to achieve a desired tension between femoral component 12 and tibial component 14. The length of prosthetic ligament 26 may also be varied.

Lateral and medial bearing components 38, 40, respectively, are positioned atop and secured to baseplate 30. Lateral and medial components 38, 40 define articulating surfaces 42, 44, respectively, that cooperate with condyles 18, 20 of femoral component 12 during knee articulation. In one exemplary embodiment, medial bearing component 40 is fixedly secured to tibial baseplate 30, such as by a snap-fit, to form a fixed medial component. Thus, in this embodiment, medial component 40, once secured to baseplate 30, is substantially prevented from moving relative to baseplate 30. In contrast, lateral bearing component 38 is secured to baseplate 30 to form a mobile bearing component. Thus, in this embodiment, lateral component 38 is moveable relative to baseplate 30 to encourage normal articulation and relative rotation between femoral component 12 and tibial component 14.

Specifically, in a normal knee joint, the femur rotates about a point that is medially offset, i.e., a point that is on the medial side of the knee joint, as the knee joint transitions between flexion and extension. As a result, lateral condyle 18 of femoral component 12 travels a substantially greater arcuate distance than medial condyle 20 of femoral component 12 along a plane extending across the proximal end of the resected proximal tibia as the knee travels between various stages of flexion and extension. In the illustrated embodiment of FIGS. 1-3, lateral condyle 18 is substantially symmetrical to medial condyle 20 in femoral component 12, and lateral component 38 is substantially symmetrical to medial component 40 in tibial component 14. The larger distance traveled by lateral condyle 18 is facilitated by fixing medial component 40 and allowing lateral component 38 to move, as described below. However, it is also within the scope of the present disclosure that asymmetrical tibial and/or femoral components may be used, such as by using relatively larger articulating surfaces on the lateral portions of the components.

As indicated above, medial component 40 of tibial component 14 is a fixed bearing component. For example, in one exemplary embodiment, articulating surface 44 may be a highly conforming articulating surface, meaning surface 44 is highly congruent with a mating structure such as medial condyle 20. As a highly conforming articular surface, articulating surface 44 has a concave shape that substantially corresponds to the convex shape of the articulating surface of medial condyle 20 of femoral component 12. As a result, the anterior and posterior movement of medial condyle 20 is controlled, while allowing for rotation of femoral component 12 atop articulating surface 44 of medial condyle 20. In this manner, the natural movement of an anatomic medial condyle with respect to an anatomic tibia is replicated by medial condyle 20 and medial component 40.

In contrast to medial component 40 of tibial component 14, lateral component 38 of tibial component 14 is a mobile bearing component. For example, in one exemplary embodiment, lateral component 38 may be advanced anteriorly as femoral component 12 transitions from extension into flexion and, correspondingly, lateral component 38 may be advanced posteriorly as femoral component 12 transitions from flexion into extension. Articulating surface 42 may be a less conforming articulating surface as compared to articulating surface 44, meaning articulating surface 42 is somewhat less congruent with the mating lateral condyle 18. As a less conforming articular surface, articulating surface 42 has a concave shape that defines a larger radial profile than lateral condyle 18 of femoral component 12. This reduced congruence allows some anterior and posterior movement of lateral condyle 18 within lateral component 38, consistent with the natural movement of an anatomic lateral condyle with respect to an anatomic tibia. Although conformity is somewhat reduced, articulating surface 42 and lateral condyle 18 still sufficiently conform to facilitate transmission of force from lateral condyle 18 to lateral component 38, with the transmitted force sufficient to drive the anterior and posterior motion of lateral component 38. Alternatively, articulating surface 42 may be a highly conforming surface similar to articulating surface 44.

Figure 2:
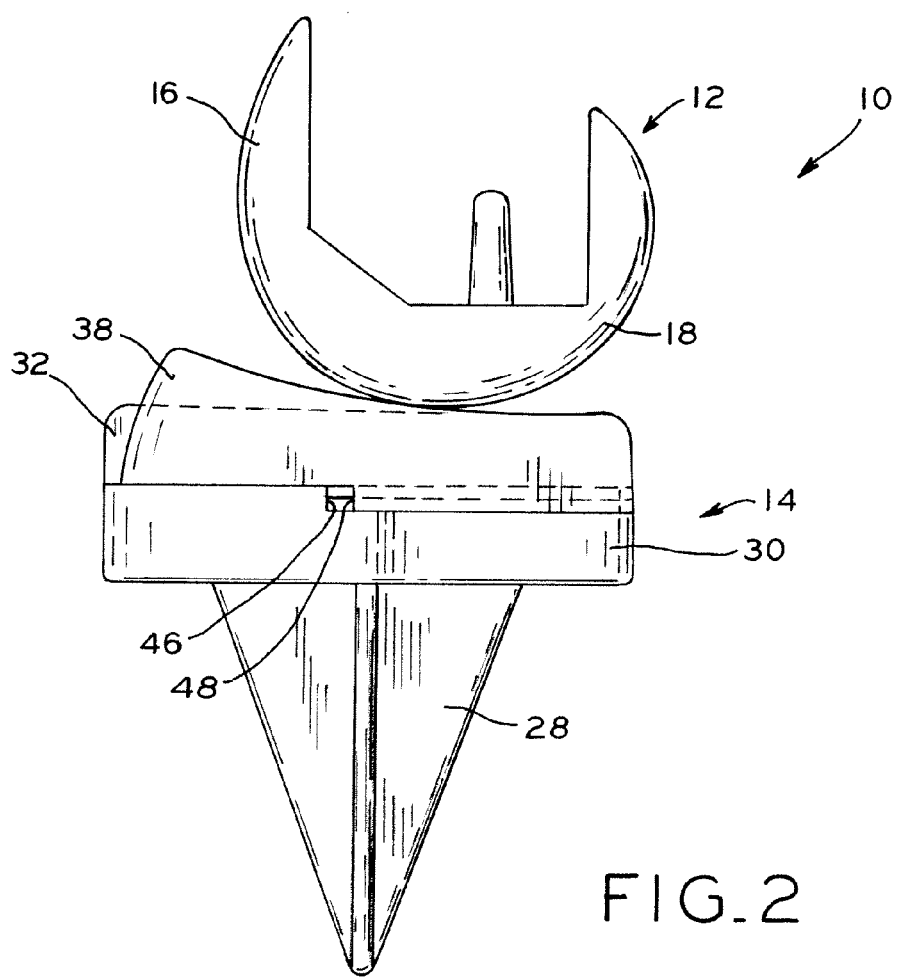
FIG. 2 is an elevational view of the total knee arthroplasty system of FIG. 1.

In one exemplary embodiment, shown in FIGS. 1-3, an anterior stop is provided to prevent lateral component 38 from subluxing anteriorally. In this embodiment, baseplate 30 includes a stepped portion that defines shoulder 46, while lateral component 38 includes a corresponding stepped portion that defines shoulder 48. As lateral component 38 is advanced anteriorally, shoulder 48 of lateral component 38 contacts shoulder 46 of baseplate 30 to prevent additional anterior movement of lateral component 38 relative to baseplate 30. Once in this position, additional flexion of femoral component 12 may result in femoral roll-off, i.e., additional movement of lateral condyle 18 in a posterior direction away from lateral component 38 of tibial component 14. Advantageously, by allowing for femoral roll-off of lateral condyle 18, total knee prosthesis system 10 more accurately replicates the natural articulation of a knee joint. To maintain the overall stability of knee arthroplasty system 10 during femoral roll-off, lateral component 38 may include a convex portion at a posterior end thereof which is adapted to cooperate with a concave posterior end formed in lateral condyle 18 during deep flexion. One exemplary knee implant with such cooperating convex and concave portions is described in U.S. patent application Ser. No. 12/694,771, filed on Jan. 27, 2010, now abandoned, and entitled LATERAL CONDYLE POSTERIOR INFLECTION FOR TOTAL KNEE IMPLANT, the disclosure of which is hereby incorporated by reference herein in its entirety.

In order to secure lateral component 38 to baseplate 30, baseplate 30 may, in one exemplary embodiment, include projection 50 having a T-shaped cross-section that is received within a corresponding groove 52 formed in lateral component 38. Due to the interaction of projection 50 with the portion of lateral component 38 defining groove 52, lateral component 38 may move anteriorly and posteriorly in the direction of double-headed arrow A of FIG. 3, but is prevented from substantial movement in a medial or lateral direction. In other exemplary embodiments, projection 50 and groove 52 may be arcuate to allow for lateral component 38 and correspondingly condyle 18 to move along an arcuate path that has an axis of rotation that is medially offset within respect to the knee joint to further replicate the natural, anatomical articulation of the knee joint.

Referring to FIGS. 5 and 6, another exemplary embodiment of tibial component 14 is shown as tibial component 54. Tibial component 54 is substantially similar to tibial component 14 and corresponding reference characters have been used to identify identical or substantially identical parts therebetween. Referring to FIG. 5, lateral component 55 of tibial component 54 includes internal groove 56, shown in dashed lines in FIG. 5, that allows for lateral component 55 of tibial component 54 to be snap-fit or otherwise secured to projection 58 of tibial baseplate 60. In this embodiment, movement of lateral component 55 relative to tibial baseplate 60 is constrained only by the interaction of internal side walls 61 and end walls 63, shown in dashed lines in FIG. 5, that define groove 52 with projection 58. For example, medial/lateral movement of lateral component 55 is substantially prevented by the interaction of sidewalls 61, shown in FIG. 6, with projection 58. However, because projection 58 has a length that is less than the length of groove 52, lateral component 55 may move in an anterior/posterior direction until one of end walls 63 that define groove 52 contact a corresponding end of projection 58. As a result of the increased length of groove 52 relative to projection 58, lateral component 55 of tibial component 54 may be configured to be advanced substantially further in an anterior direction than lateral component 38 of tibial component 14.

Additionally, due to the ability to configure lateral component 55 to move further in an anterior direction than lateral component 38, a highly conforming articulating surface may be formed on lateral component 55. In this embodiment, as condyle 18 of femoral component 12 moves in a posterior direction as the knee joint transitions from extension to flexion, lateral component 55 would move in a posterior direction with condyle 18. Similarly, as condyle 18 of femoral component 12 moves in an anterior direction as the knee joint transitions from flexion to extension, lateral component 55 would move in an anterior direction with condyle 18. By having lateral component 55 of tibial component 54 move with condyle 18 of femoral component 12, condyle 18 may advance further in a posterior direction than can be achieved with known femoral components.

In yet another exemplary embodiment (not shown), a lateral component similar to lateral components 42, 55 may not have any restriction on movement in the anterior or posterior directions. Thus, the lateral component may be adapted to slide in a linear or arcuate path without any shoulders or end walls preventing the lateral component from further motion along the path.

As discussed in detail above, prosthetic ligament 26, shown in FIGS. 1 and 4, may be secured to femoral component 12 and tibial component 14. By utilizing prosthetic ligament 26, movement of femoral component 12 and tibial component 14 relative to one another is restricted. The specific restriction in the movement of femoral component 12 and tibial component 14 relative to one another that is created by prosthetic ligament 26 may be designed to replicate the restrictions imposed on movement of a natural knee joint by the cruciate ligaments. However, as shown in FIG. 2, knee arthroplasty system 10 may also be used without prosthetic ligament 26.

In still another alternative, only one of the two cruciate ligaments in a natural knee is replicated using prosthetic ligament 26. For example, a partial or total knee arthroplasty may utilize fixed medial component 40 and/or mobile lateral component 38, while still retaining one or both of the natural cruciate ligaments. In one exemplary embodiment shown in FIG. 9B, tibial component 14 may be designed for surgeries in which both the posterior cruciate ligament (PCL) and the anterior cruciate ligament (ACL) are resected, but only the PCL is replaced with one or more prosthetic ligaments 26. In this "cruciate retaining" design, lateral component 40 and medial component 38 may be joined by bridge 39. Alternatively, a partial knee arthroplasty may be performed in which only a single side of the natural tibial plateau is replaced, so that either medial component 40 or lateral component 38 may be used to replace a resected articular surface on the medial or lateral side of the tibia, respectively.

In another exemplary embodiment, shown in FIG. 7, a pair of prosthetic ligaments 62 is shown. Referring to FIG. 7, each of prosthetic ligaments 62 includes opposing spherical heads 66 and elongate body 68 extending between opposing heads 66. In an exemplary embodiment, spherical heads 66 are resiliently deformable and are sized to be received within corresponding spherical grooves 70 provided at attachment points 72, 74 that may formed on tibial component 14 and femoral component 12, respectively. The spherical shape of heads 66 and grooves 70 allow heads 66 to articulate with grooves 70 as femoral component 12 and tibial component 14 move relative to one another. By securing prosthetic ligaments 62 to femoral component 12 and tibial component 14, as shown in FIG. 7, the function of the anterior and posterior cruciate ligaments may be replicated by prosthetic ligaments 62. However, heads 66 may be rigid or non-resilient, and need not articulate with attachment points 72, 74. For example, heads 66 may be formed of a solid material, and/or may be fixedly or permanently attached to attachment points 72, 74. For example, in some embodiments, prosthetic ligaments 62 may be sufficiently flexible to obviate the benefits of spherical heads 66 and spherical grooves 70.

As shown in FIG. 7, attachment points 72 of tibial component 14 are spaced apart from one another in both an anterior/posterior dimension and a medial/lateral dimension. Thus, in one exemplary embodiment, the anterior most attachment point 72 is positioned on the lateral side of tibial component 14, while the posterior most attachment point 72 is positioned on the medial side of tibial component 14. Referring to attachment points 74 on femoral component 12, attachment points 74 are formed in opposing lateral and medial condyles 18, 20.

In one exemplary embodiment, ligaments 62 are formed as solid, flexible ligaments. In one exemplary embodiment, a plurality of ligaments 62 each having a different stiffness is provided. By providing a plurality of ligaments 62 each having a different stiffness, a surgeon may select an appropriate stiffness of ligaments 62 to create a condition in which their crossing interactions drive axial rotation of a femoral component upon a tibial component during knee articulation. Moreover, ligaments 62 can be selected based on a variety of ligament material properties to provide optimal joint kinematics and soft tissue balance, as discussed in detail below.

In another exemplary embodiment, a locking mechanism (not shown) may be attached to femoral component 12 and/or tibial component 14 to lock spherical heads 66 of prosthetic ligaments 62 in position within spherical grooves 70. Additionally, while described as having spherical head 66 and elongate body 68, prosthetic ligaments 62 may be connected to femoral component 12 and tibial component 14 in any suitable manner.

Additionally, in order to replicate the function of individual natural cruciate ligaments, a plurality of prosthetic ligaments 62 may be used. This provides the surgeon with an increased ability to reconstitute the function of the natural cruciate ligaments, such as by adjusting the flexion/extension balance of the knee joint and/or the anterior/posterior contact point of femoral component 12 on tibial component 14. By using multiple ligaments, the natural structure and function of the natural anterior cruciate ligament (ACL) and/or posterior cruciate ligament (PCL) is more closely approximated, with different fibers potentially supporting loads that vary throughout the range of motion.

Figure 8:
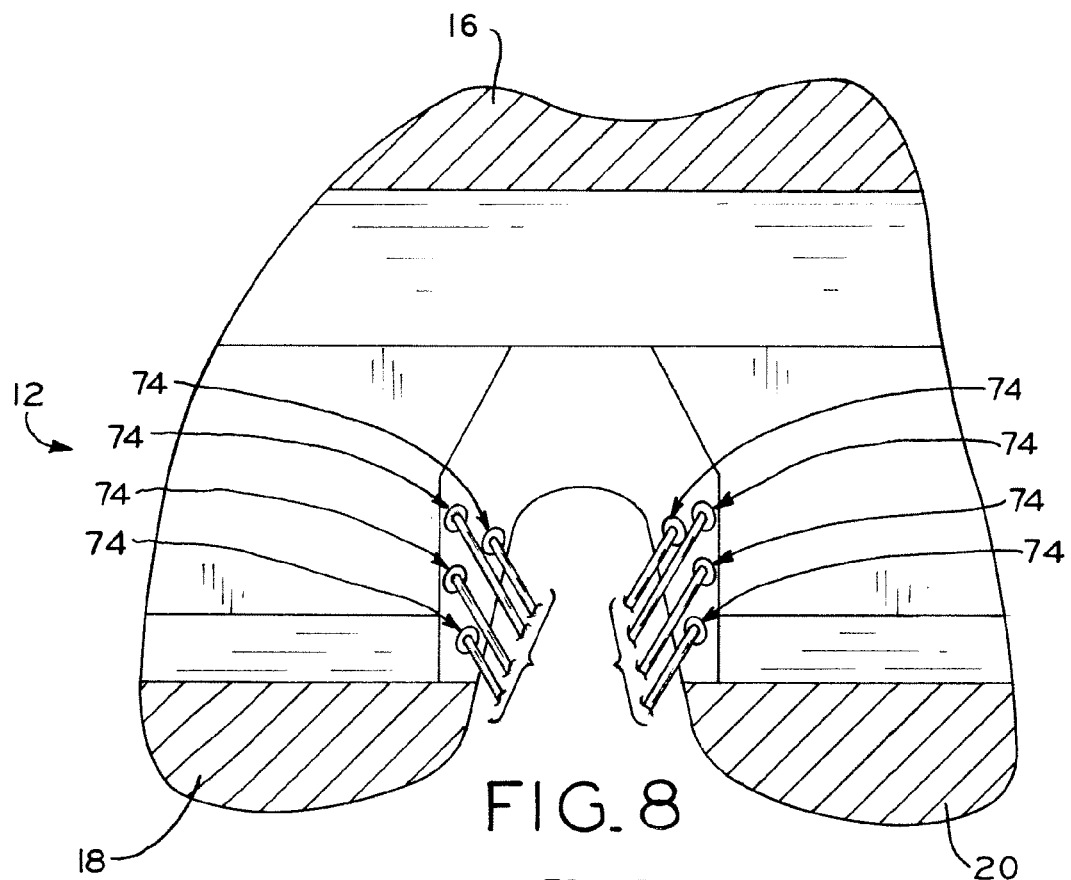
FIG. 8 is a cross-sectional, plan view of a femoral component according to another exemplary embodiment depicting a plurality of prosthetic ligaments connected thereto.
Figure 9A:
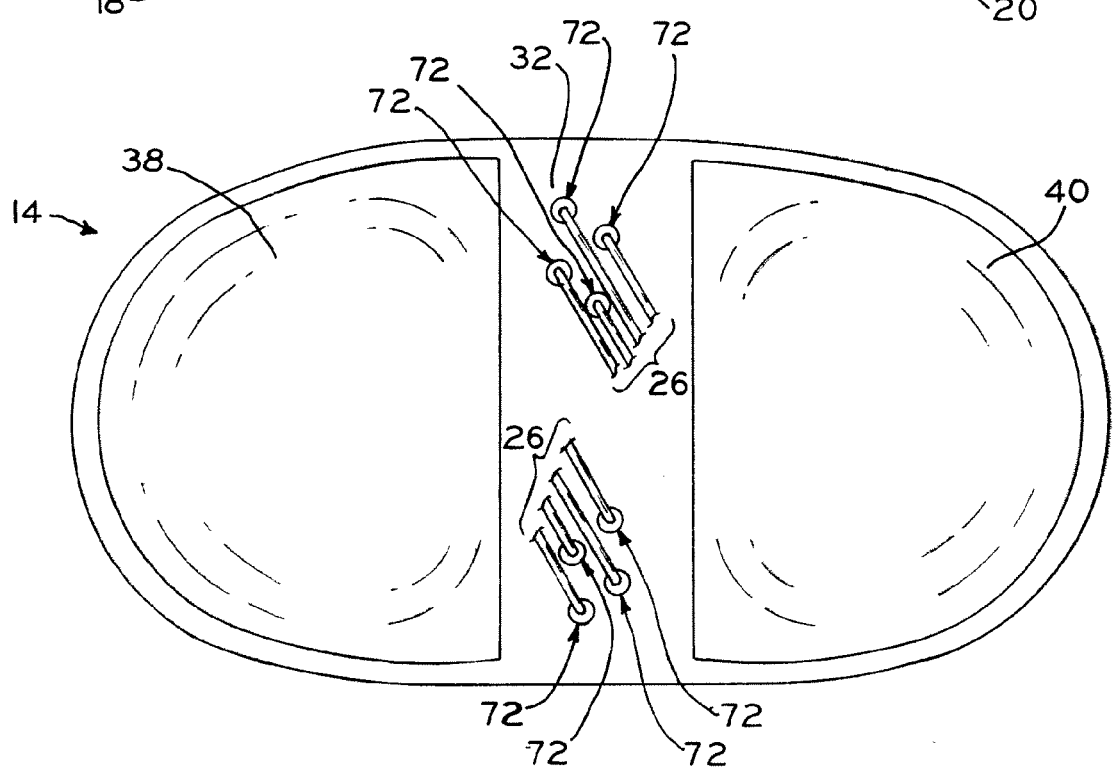
FIG. 9A is a plan view of tibial component according to another exemplary embodiment depicting a plurality of prosthetic ligaments connected to anterior and posterior sides thereof.

Referring to FIGS. 8 and 9A, a plurality of attachment points 72, 74 are shown on tibial component 14 and femoral component 12. In use, a surgeon may attach one of spherical heads 66 of a first ligament 62 to one of attachment points 74 on femoral component 12 and then attach the opposing spherical head 66 to one of attachment points 72 on tibial component 14. Then, the surgeon may trial the knee joint, i.e., actuate the patient's knee joint through flexion and extension. Based on the surgeon's observations during the trialing, the surgeon may determine that use of a different attachment point 72, 74 for at least one of spherical heads 66 of one of ligaments 62 may provide a more natural, anatomical articulation of the knee joint for an individual patient or that the use of an additional prosthetic ligament 62 may be advantageous.

If the surgeon does determine that a different attachment point 72, 74 would be beneficial for the patient, the surgeon may then remove one of spherical heads 66 of one of prosthetic ligaments 62 from its attachment point 72, 74 and position it within another attachment point 72, 74. The range of motion testing may then be repeated to determine if a proper flexion/extension balance of the knee joint and/or the anterior/posterior contact point of femoral component 12 on tibial component 14 has been achieved. If the articulation of the knee joint is still not satisfactory to the surgeon, one of spherical heads 66 may be removed by attachment points 72, 74 and placed at another of attachment points 72, 74. This process may be repeated as necessary until the surgeon has found positions for ligaments 26 that most accurately replicates the natural, anatomical articulation of the knee joint. The illustrated embodiment of FIGS. 8 and 9A show attachment points 72, 74 for prosthetic ligaments 62 arranged in a similar fashion to the arrangement of natural anatomic ligaments. However, the orientation of attachment points can have different patterns or orientations within the scope of the present disclosure, such as an orientation that is a reverse or mirror of the illustrated orientation.

In another exemplary embodiment (not shown), a prosthetic ligament may be provided that includes a central body portion with a plurality of necks extending from the central body portion, such as in a "Y" configuration where two necks extend from the central body portion or a "pitchfork" configuration where three necks extend from the central body portion. In addition, each of the necks may terminate at a spherical head 66, which may be secured to one of attachment points 72, 74 in a substantially similar manner as described in detail above with respect to prosthetic ligaments 62. Additionally, in this embodiment, the prosthetic ligament may be attached at a plurality of attachment points 72, 74 on each of and/or one of femoral component 12 and tibial component 14. In this manner, additional variability may be introduced into total knee prosthesis system 10 to allow for a more precise adjustment of the articulation of the knee joint, as discussed below.

Referring to FIGS. 10 and 11, another exemplary embodiment of prosthetic ligaments 62 are shown as prosthetic ligaments 76. Prosthetic ligaments 76 may be substantially permanently secured to dovetail inserts 78, 80. Dovetail inserts 78, 80 are configured to be received in corresponding dovetail grooves 82, 84, formed in tibial component 14 and femoral component 12, respectively. In this manner, prosthetic ligaments 76 may be preattached and readily positioned within or removed from femoral prosthesis system 10. In another exemplary embodiment, prosthetic ligaments 76 are not substantially permanently attached, but are readily removable from dovetail inserts 78, 80. In this embodiment, prosthetic ligaments 76 may be removed from and/or added to dovetail inserts 78, 80 to provide a desired configuration for an individual patient's knee joint. For example, a plurality of prosthetic ligaments 76 may be provided in which each prosthetic ligament 76 has a different characteristic or a combination of different characteristics. For example, each prosthetic ligament 76 may have a different stiffness and/or different length than other prosthetic ligaments 76, or may be made of a different material. In this manner, a surgeon may select a prosthetic ligament 76 that has the characteristics that allows for the most accurate replication of the natural, anatomical articulation of the patient's knee joint.

While described in detail above as having a specific design, including spherical heads and elongate bodies, prosthetic ligaments 26, 62, 76, may take a number of different forms. For example, instead of being formed as a solid, flexible prosthetic ligament and providing a variety of different thicknesses, prosthetic ligaments 26, 62, 76 may be woven or rope-like in order to determine the passive envelope of soft tissue in the knee joint and to provide anterior/posterior translation limits for the femur upon the tibia.

Additionally, variable properties of prosthetic ligaments 26, 62, 76 may be manipulated to allow the surgeon to optimize the kinematics and feel of the knee prosthesis, e.g., by providing tight ligaments for joint stability and loose ligaments for joint laxity. Examples of such properties include: the number of prosthetic ligament strands in a multi-strand design; the size or diameter of prosthetic ligament strands; the material from which the prosthetic ligament is made; the length and/or tension of the prosthetic ligament within the knee prosthesis; the orientation of fibers relative to one another, i.e. a "Y" oriented fiber as discussed above; and the location of attachment of prosthetic ligament strands, also discussed above. The surgeon may vary these or other characteristics of prosthetic ligaments 26, 62, 76 for an individual patient to better match the needs of the patient, and to compensate for differently shaped femurs, different genders, different expected level of athletic abilities and activities, and/or different ages between patients.

Moreover, varying the properties of prosthetic ligaments 26, 62, 76 provides an opportunity for the surgeon to balance the soft tissues of the knee, and to reproduce as closely as possible the function of the natural cruciate ligaments. Further, several ligament properties can be varied intra-operatively. For example, a surgeon may vary the lengths of prosthetic ligaments 26, 62, 76 at the time of implantation, such as by trimming a portion of the ligament to create the desired length and tension. A cut-to-length prosthetic ligament 26, 62, 76 may be pre-attached to either femoral component 12 or tibial component 14, so that only one end of prosthetic ligament needs to be cut to length upon attachment to the other component. Similarly, in the multi-strand design shown in FIGS. 8 and 9A, strands having different properties can be added, removed or substituted until the desired soft tissue balance and joint kinematics are achieved.

Figure 12:
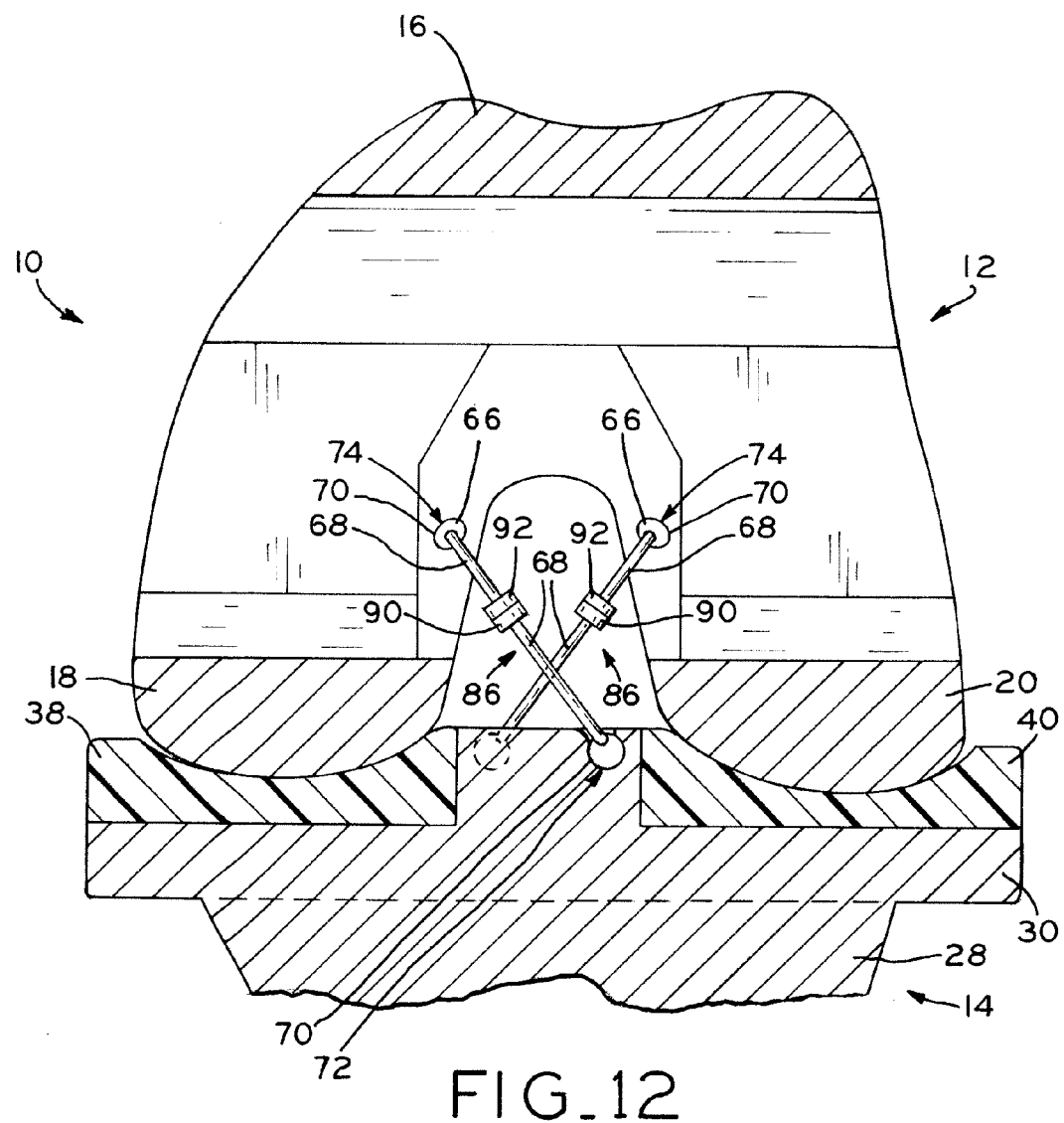
FIG. 12 is a cross-sectional view of a total knee arthroplasty system according to another exemplary embodiment depicting a femoral component at 90 degrees of flexion with respect to the tibial component, wherein the cross-section is taken in a medial/lateral direction that is slightly posterior relative to the total knee arthroplasty system, and in which provisional prosthetic ligaments according to an exemplary embodiment are also depicted.

Referring to FIG. 12, provisional prosthetic ligaments 86 are shown. Provisional prosthetic ligaments 86, 88 are substantially similar to prosthetic ligaments 62, and corresponding reference numerals have been used to identify identical or substantially identical parts therebetween. As shown in FIG. 12, elongate bodies 68 of provisional prosthetic ligaments 86 are divided into two individual sections connected to one another by opposing attractive magnets 90, 92. In this embodiment, the force required to separate magnets 90, 92 is known and is selected to be at a level above which the total knee arthroplasty system 10 would be considered to be too tight during articulation. Thus, if system 10 is too tight, then, during range of motion testing, magnets 90, 92 will separate from one another and provide immediate visual and tactile feedback to a surgeon indicating that the knee joint is too tight.

As an alternative to magnets 90, 92, provisional prosthetic ligaments 86 may be designed such that elongate bodies 68 fail upon the application of a force in excess of a predetermined limit, either along the extent of elongate body 68 or at one end thereof. For example, elongate body 68 may have a weakened portion of known failure strength, or the entirety of elongate body 68 may have a known failure strength. Alternatively, the moorings between elongate body 68 and femoral component 12 and/or tibial component 14 (such as at spherical heads 66) may have a weakened portion or known failure strength. Thus, if the joint is too tight, elongate bodies 68 of provisional prosthetic ligaments 86 will fail by either breaking or releasing from their moorings on femoral component 12 and/or tibial component 14, which will also provide immediate visual and tactile feedback to the surgeon indicating that the joint is too tight. Prosthetic ligaments 86 utilizing magnets or breakage allow an indirect measurement of tension therein, in that an unbroken prosthetic ligament signifies that tension is below the breakage threshold and a broken prosthetic ligament signifies a tension above the breakage threshold.

A further alternative for provisional prosthetic ligaments 68 may include coupling instrumentation to one or more of ligaments 68 to provide data feedback on the level of strain and/or force being experienced by ligaments 68. For example, a strain gauge may be coupled to a provisional prosthetic ligament 68 of known elasticity, so that a given increase in length of the strain gauge is known to correspond to a given force. Prosthetic ligaments 86 utilizing data feedback allow direct measurement of tension therein, so that the tension at any given flexion may be measured.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A prosthetic knee system, comprising:
   a femoral component having a lateral condyle and a medial condyle, said femoral component defining a plurality of femoral attachment points between said lateral and medial condyles, said plurality of femoral attachment points comprising at least one of a plurality of lateral femoral attachment points and a plurality of medial femoral attachment points;
   a tibial component having a lateral articulating surface, a medial articulating surface, and a center region located between said lateral articulating surface and said medial articulating surface, said tibial component defining a plurality of tibial attachment points on said center region comprising at least one of a plurality of anterior tibial attachment points on said center region and a plurality of posterior tibial attachment points on said center region; and
   a first prosthetic ligament having an elongate body, a first end, a second end, and attachable to any of said plurality of femoral attachment points, said elongate body also attachable to any of said plurality of tibial attachment points, said first prosthetic ligament extending from one of said plurality of femoral attachment points to one of said plurality of tibial attachment points to define a prosthetic ligament span, said prosthetic ligament span defining a prosthetic ligament tension, wherein said prosthetic ligament tension is variable when said first and second ends of said prosthetic ligament are attached to varying ones of said plurality of femoral attachment points and said plurality of tibial attachment points.

2. The prosthetic knee system of claim 1 comprising a second prosthetic ligament, said femoral component having a lateral femoral attachment point and a medial femoral attachment point, said tibial component having an anterior tibial attachment point on said center region and a posterior tibial attachment point on said center region, said first prosthetic ligament extending from said anterior tibial attachment point to one of said medial femoral attachment point and said lateral femoral attachment point, said second prosthetic ligament extending from said posterior tibial attachment point to the other of said medial femoral attachment point and said lateral femoral attachment point.

3. The prosthetic knee system of claim 1, wherein at least one of said first end and said second end of said first prosthetic ligament comprises a spherical head, at least one of said femoral attachment point and said tibial attachment point comprising a spherical groove, said spherical head receivable within said spherical groove to lock said first prosthetic ligament to at least one of said femoral component and said tibial component.

4. The prosthetic knee system of claim 1, further comprising a dovetail insert, said first prosthetic ligament affixed to said dovetail insert, at least one of said femoral component and said tibial component including a dovetail groove sized to receive said dovetail insert, said first prosthetic ligament attached to one of said femoral component and said tibial component when said dovetail insert is received in said dovetail groove.

5. The prosthetic knee system of claim 1, wherein said first prosthetic ligament comprises a means for severing the connection between said first prosthetic ligament and one of said femoral component and said tibial component.

6. The prosthetic knee system of claim 5, wherein said means for severing comprises at least one of: i) a pair of cooperating magnets disposed between said first end and said second end of said first prosthetic ligament; ii) a weakened portion along a portion of said elongate body of said first prosthetic ligament; iii) a connection between said first prosthetic ligament and one of said femoral component and said tibial component; and iv) a break strength of said elongate body of said first prosthetic ligament.

7. The prosthetic knee system of claim 1, wherein said center region extends from an anterior side to a posterior side of said tibial component.

8. The prosthetic knee system of claim 1, wherein said tibial component further comprises a bridge located between and joining said lateral articulating surface and said medial articulating surface.

9. The prosthetic knee system of claim 1, wherein said plurality of femoral attachment points of said femoral component comprises:
 a plurality of lateral femoral attachment points located on an inner side of said lateral condyle; and
 a plurality of medial femoral attachment points located on an inner side of said medial condyle.

10. A prosthetic knee system, comprising:
 a femoral component having a lateral condyle and a medial condyle, said femoral component defining at least one femoral attachment point;
 a tibial component having a lateral articulating surface and a medial articulating surface, said tibial component defining at least one tibial attachment point;
 at least one prosthetic ligament having an elongate body, a first end, and a second end, said first end attachable to said femoral attachment point of said femoral component and said second end attachable to said tibial attachment point of said tibial component, whereby said femoral component is coupled with said tibial component when said first prosthetic ligament is attached to said femoral attachment point and said tibial attachment point; and
 means for intraoperatively selecting a tension in said at least one prosthetic ligament.

11. A prosthetic knee system, comprising,
 a femoral component having a lateral condyle and a medial condyle, said femoral component defining a plurality of femoral attachment points comprising at least one of a plurality of lateral femoral attachment points and a plurality of medial femoral attachment points;
 a tibial component having a lateral articulating surface and a medial articulating surface, said tibial component defining a plurality of tibial attachment points comprising at least one of a plurality of anterior tibial attachment points and a plurality of posterior tibial attachment points;
 a first prosthetic ligament having an elongate body, attachable to any of said plurality of femoral attachment points, said elongate body also attachable to any of said plurality of tibial attachment points, said first prosthetic ligament extending from one of said plurality of femoral attachment points to one of said plurality of tibial attachment points to define a prosthetic ligament span, said prosthetic ligament span defining a prosthetic ligament tension, wherein said prosthetic ligament tension is variable when first and second ends of said prosthetic ligament are attached to varying ones of said plurality of femoral attachment points and said plurality of tibial attachment points; and
 a second prosthetic ligament, said femoral component having a lateral femoral attachment point and a medial femoral attachment point, said tibial component having an anterior tibial attachment point and a posterior tibial attachment point, said first prosthetic ligament extending from said anterior tibial attachment point to one of said medial femoral attachment point and said lateral femoral attachment point, said second prosthetic ligament extending from said posterior tibial attachment point to the other of said medial femoral attachment point and said lateral femoral attachment point.

12. The prosthetic knee system of claim 11, wherein at least one of said first end and said second end of said first prosthetic ligament comprises a spherical head, at least one of said femoral attachment point and said tibial attachment point comprises a spherical groove, said spherical head receivable within said spherical groove to lock said first prosthetic ligament to at least one of said femoral component and said tibial component.

13. The prosthetic knee system of claim 12, wherein said second prosthetic ligament has an elongate body, a first end and a second end, and at least one of said first end and said second end comprises a spherical head receivable within said spherical groove of said tibial attachment point to lock said second prosthetic ligament to at least one of said femoral component and said tibial component.

* * * * *